United States Patent [19]
Bronson

[11] Patent Number: 5,256,539
[45] Date of Patent: Oct. 26, 1993

[54] METHOD OF SCREENING FOR INFERTILITY OF SPERM

[75] Inventor: Richard A. Bronson, Huntington, N.Y.

[73] Assignee: The Research Foundation of State University of New York, Albany, N.Y.

[21] Appl. No.: 740,042

[22] Filed: Aug. 1, 1991

[51] Int. Cl.⁵ ............................................. C12Q 1/02
[52] U.S. Cl. ................................. 435/7.21; 435/7.1; 435/7.2; 435/29
[58] Field of Search ................... 435/29, 7.1, 7.2, 7.21

[56] References Cited

U.S. PATENT DOCUMENTS

| | | |
|---|---|---|
| 3,660,558 | 5/1972 | Ericsson . |
| 4,683,213 | 7/1987 | Ax . |
| 4,767,703 | 8/1988 | Ax et al. . |
| 4,894,326 | 1/1990 | Matsuura . |
| 4,894,328 | 1/1990 | Alderete et al. . |
| 4,980,279 | 12/1990 | Peters et al. . |
| 4,999,283 | 3/1991 | Zavos et al. . |

OTHER PUBLICATIONS

Bronson, R. A., "Evidence that an ARG-GLY-ASP Adhesion Sequence Plays a Role in Mammalian Fertilization", pp. 1019-1025 (1990).
Bronson, R. A., "Sperm-oolemmal Interaction: Role of the ARG-GLY-ASP (RGD) Adhesion Peptide", pp. 527-529 (Sep. 1990).
Bronson, R. A., "Capacitated Human Spermatozoa Display Fibronection (Fn) on Their Surface and Anti--Fn Antibodies Inhibit Penetration of the Zona-3 Hamster Eggs by Human Sperm", (Apr. 24-27, 1991).
Yasuzumi et al. Chem. Abst. vol. 100 (1984) p. 20987p.
Vuento et al. Chem. Abst. vol. 101 (1984) p. 107916j.

Primary Examiner—Sam Rosen
Attorney, Agent, or Firm—Hoffmann & Baron

[57] ABSTRACT

A method for detecting the presence of infertility in mammalian male animals based upon failure of sperm to undergo successful capacitation. Sperm samples are given the opportunity to undergo capacitation and subsequently contacted with antibodies to fibronectin. Binding levels indicate the degree of capacitation and consequently the presence of infertility.

10 Claims, No Drawings

METHOD OF SCREENING FOR INFERTILITY OF SPERM

FIELD OF INVENTION

The present inVention relates to methods of screening for infertility in mammalian male test animals. More specifically, the present invention relates to methods for detecting a lack of capacitation in a sample of spermatozoa from a test male mammal. In particular, the present invention relates to diagnostic assays using antibodies to fibronectin to detect a lack of capacitation in a sample of human spermatozoa due to disorders related to fibronectin expression on the sperm surface.

BACKGROUND OF THE INVENTION

It is often useful to be able to predict the fertility of a mammalian male animal in a variety of contexts. For example, animal breeders typically go to great lengths to find male animals likely to produce offspring having desirable genetic traits. However, animal breeding is often an expensive endeavor and males having low fertility are of reduced value due to the increased cost of breeding the animal where repeated inseminations are required to ensure impregnation. Currently, there are few reliable methods for detecting a lack of fertilizing capacity in these male animals short of statistical data compiled on their past breeding results.

Additionally, the medical community is often concerned with human fertility but has few reliable methods for evaluating the fertility of male patients. In particular, physicians have few reliable methods for detecting a lack of capacitation in the sperm of a patient.

Mammalian spermatozoa in semen cannot fertilize eggs but must undergo alterations in the plasma membrane in order to acquire fertilizing capability. The process during which the spermatozoa undergo these alterations in their membrane is termed capacitation and occurs naturally in the female reproductive tract once the sperm has been deposited.

Capacitation refers to the ability of sperm to adhere to, penetrate and fertilize susceptible ova. Penetration and fertilization not only requires potentiality of the sperm to achieve a functional status but also requires that favorable conditions exist in the uterine environment. If favorable conditions exist in the mammalian uterus, sperm become capacitated, penetrate the ova and embryonic development begins.

It has recently been discovered that certain synthetic fibronectin-derived polypeptides containing the tripeptide, Arginine-Glycine-Aspartate, in their cell binding domains will competitively inhibit sperm-oolemal adhesion and penetration of hamster ova contacted with either human or hamster sperm that has undergone successful capacitation. Further evidence has been obtained that receptors for proteins, such as fibronectin, which contain the tripeptide, Arg-Gly-Asp, exist on the surface of mammalian eggs. Consequently, it has been postulated that fibronectin expression on the spermatozoan surface might play an important role in the adhesion and penetration of sperm to susceptible ova. Previously, the nature of the role of fibronectin has remained unclear.

Fibronectin plays a wide role in diverse processes, ranging from immune adherence of microbes to connective tissue remodelling and embryogenesis. For example, fibronectin has been found in heavy accumulations in vivo at sites of tissue inflammation and injury. Fibronectin is a high molecular weight glycoprotein homodimer, consisting of two identical chains (Mr=220-250,000), connected by disulfide bridges which can exist in two forms, plasma fibronectin, which is soluble, and cellular fibronectin, which is insoluble. Limited proteolytic digestion of cellular fibronectin has revealed several domains with different binding affinities for collagen, fibrinogen and heparin, in addition to the cell binding domain. The cell binding domain of fibronectin, as well as other extracellular matrix proteins such as collagen Type I, Type IV and laminin, have been shown to possess the tripeptide sequence previously mentioned, Arginine-Glycine-Aspartate.

It has now been discovered that there is significant increase in the presence of fibronectin on the surface of capacitated mammalian sperm as compared with fresh mammalian sperm which has not undergone capacitation. As a result, it has now been postulated that detecting the presence of fibronectin expressed upon the surface of the sample of mammalian sperm is a good indicator of whether the sperm has undergone successful capacitation.

It is therefore an object of the present ineention to provide an improved method for detecting the presence of infertility in a mammalian male test animal using antibodies to fibronectin.

It is a further object of the present invention to provide a method for detecting a lack of capacitation in a sample of sperm from a mammalian male test animal using antibodies to fibronectin.

Finally, it is an object of the present invention to provide a method for using fibronectin antibodies to detect a lack of capacitation in a sample of human spermatozoa due to disorders related to fibronectin expression on the sperm surface.

SUMMARY OF THE INVENTION

The present invention is a method for detecting the presence of infertility in mammalian males, especially humans, due to a lack of capacitation. The method involves exposing a sample of sperm from the donor subject to in vitro conditions that are favorable for inducing capacitation for a period of time sufficient for capacitation to occur. In other words, the sperm sample must be provided with sufficient opportunity to undergo its potential for capacitation.

After the sperm sample has been given sufficient opportunity to undergo capacitation, the sample is contacted with one or more monoclonal or polyclonal antibodies to fibronectin for a sufficient period of time and under conditions suitable for permitting the antibody to bind to the sperm surface. Subsequently, an evaluation and determination of the degree of antibody binding may be performed in order to detect a lack of capacitation.

Previously, there have been no reliable methods for determining the fertilizing capability of the sperm of a test subject. Although it is postulated that a variety of factors probably play a role in promoting this fertilizing capability, it is generally accepted that successful capacitation of the sperm is one of those factors.

The present invention affords an improved method for detecting a lack of capacitation, especially where insufficient capacitation is a result of disorders involving the expression of fibronectin on the sperm surface. Consequently, the present invention will afford physicians a well as veterinarians as useful tool in diagnosing fertility problems.

For a better understanding of the present invention, together with other and further objects, reference is made to the following description, the scope of which will be pointed out in the appended claims.

DETAILED DESCRIPTION

In accordance with the preferred embodiment of the method of the present invention, a semen sample is obtained from the test subject. Subsequently, an acceptable separation and isolation procedure is performed to separate the sperm component from the seminal vehicle. Although the following embodiments are illustrated in terms of a human sperm sample, the method of the present invention is equally applicable to sperm samples of other mammalian species with the exception of minor modifications where indicated.

For example, an acceptable approach for separation and isolation includes injecting 300 microliters of semen under 2 milliliters of Biggers-Whitten-Whittingham (BWW) medium containing 5 mg/ml of serum albumin, preferably obtained from the same genus and species as the test subject. A 100 milliliter preparation of BWW should include 490.2 mg NaCl, 35.6 mg KCl, 16.2 mg $KH_2PO_4$, 29.4 mg $MgSO_4$, 2.8 mg sodium pyruvate, 100 mg dextrose, 300 mg $NaHCO_4$, 52.7 mg calcium lactate, 0.368 sodium lactate, 7.5 mg penicillin G, 7.5 mg streptomycin sulfate and 0.02% phenol red.

The medium containing the semen sample is subsequently incubated for 60 minutes at 37° C. under an air mixture having a 5% $CO_2$ component. Following incubation, the mixture containing motile sperm is collected and centrifuged at 600 g's and the sperm component is resuspended to a concentration of $20 \times 10^6$ cells/ml using BWW medium having a serum albumin concentration of 30 mg/ml. If sperm samples from other mammalian species are to be isolated the appropriate modifications to the medium for capacitating sperm should be incorporated accordingly.

Upon completion of the separation and isolation step, the sperm sample is exposed to in vitro conditions sufficient for inducing capacitation. Inducing successful capacitation in vitro requires the presence of a sufficient amount of serum albumin in contact with the sperm sample. These amounts may differ according to the concentration of the sperm and the species from which the sample is obtained, however, this amount is readily calculated from existing data available to those in the art.

For example, at concentrations ranging from $5 \times 10^6$ cells/ml to $20 \times 10^6$ cells/ml, human sperm generally requires exposure to human serum albumin in concentrations ranging from about 5 mg/ml to about 30 mg/gl.

An example of one acceptable protocol for inducing capacitation involves incubating the sperm sample overnight at 37° C. under air having a 5% $CO_2$ component. Alternatively, the period of incubation can be shortened by increasing the osmolality of the medium from 385 to 410 mOsm.

Upon completio of the incubation for inducing capacitation, the treated sperm sample is subsequently immunoreacted with appropriate antibodies to fibronectin. While it would be acceptable to independently develop monoclonal or polyclonal antibodies to fibronectin using established and readily available immunological protocols, the preferred embodiment of the present invention utilizes two commercially available antibodies and one non-commercial antibody when the method of the present invention is being used for screening human sperm.

One of the preferred, commercially available antibodies mentioned above is F-1509, a goat-derived polyclonal antibody to human plasma fibronectin obtained from Sigma Chemical Co. in a stock concentration of 6.5 mg/ml. The second antibody is a murine IgGI monoclonal antibody to human plasma fibronectin, FN-15, and is also obtained from Sigma Chemical Co. in a stock concentration of 5 mg/ml. The third antibody is a noncommercial murine monoclonal antibody directed to human cellular fibronectin and is denoted as A134. It can be obtained from ADEZA Biomedioal in Sunnyvale, CA.

In cases where the present invention is utilized to screen other species of mammalian sperm to detect a lack of capacitation, it is preferential to either obtain or manufacture antibodies to cellular or plasma fibronectin that has been specifically isolated from the species to be screened, especially if a reliable level of specificity is to be maintained. Some commercial antibodies to fibronectin are also available for evaluating the sperm of other mammalian species.

For example, if an investigator desired to screen bull semen in order to detect a low level of capacitation, it would be preferential to use antibodies that had been directed specifically to bovine fibronectin.

In the preferred embodiment of the present invention, the immunoreaction is conducted over a three hour period at 37° C. under air having a 5% $CO_2$ component. Additionally, the ratio of sperm to antibody should be calculated based upon the titre of the antibody used, the number of fibronectin molecules on the individual spermatozoan and the number of epitopic sites recognizing the antibody used. For human sperm, for example, at a concentration ranging from about $1 \times 10^6$ motile sperm/mL to about $4 \times 10^6$ motile sperm/mL, the antibody concentration should be about 20 mg/mL to about 200 mg/ml.

EXAMPLE 1

Each of 3 separate aliquots containing 190 microliters of human spermatozoa (concentration = $20 \times 10^6$ cells/ml), which had previously been exposed to sufficient in vitro conditions for inducing capacitation, were initially exposed for three hours at 37° C. under air having a 5% $CO_2$ component to 10 microliters of each of the aforementioned antibodies, FN-15, F-1509 and A134, respectively. Monoclonal antibody FN-15 and polyclonal antibody F-1509 were tested at several dilutions, ranging from 1:20 to 1:2000.

Alternatively, each sample can be immunoreacted with a combination of polyclonal and monoclonal antibodies directed to fibronectin as long as the subsequent steps involved in determining the binding status of the antibodies to the sample incorporate an appropriate combination of secondary antibodies to ensure accurate detection of binding.

For example, if murine and bovine antibodies to human plasma fibronectin are co-incubated with a human sperm sample to increase the sensitivity of the assay, appropriate anti-bovine and anti-murine secondary antibodies must be incorporated so that detectable immunocomplexes can be formed. However, it should be noted that the greater the number of different fibronectin antibodies contacting the sperm sample, the greater the chance for non-specific cross reactivity.

Consequently, when several different antibodies are used per sample, proper controls should be implemented to alert the investigator to any problems with cross reactivity.

Once the co-incubation of the sperm sample and the antibody has been completed, the resulting sperm-antibody complex is washed of any free antibody and resuspended in phosphate buffered saline (PBS) containing serum albumin, prior to the addition of secondary antibodies used in the detection and determination of antibody binding.

EXAMPLE 2

One hundred microliters of each of the sperm/antibody suspensions produced in Example 1 was placed in a Beckman E Microcentrifuge where the antibody-labelled sperm were pelleted at 12,000 rpm for 8 seconds and the medium containing the free antibodies was collected and removed. Each pellet was resuspended in 100 microliters of PBS containing 5 mg/ml of bovine serum albumin (BSA). The wash procedure was repeated twice thereafter.

After the sperm has been washed free of any unbound antibodies to fibronectin, detection and determination of bound antibody is performed in order to assess whether there is alack of capacitation as indicated by a low level of anti-fibronectin antibody binding.

In the preferred embodiment of the method of the present invention, immunofluorescence and immunobead binding techniques are used. In particular, these techniques allow an investigator to score individual spermatozoa in order to determine the proportion of sperm expressing fibronectin on their surface. Although other immunological detection methods may work as effectively, it is important to note that the method selected must provide for accurate scoring of the sperm if reliable quantitative binding results are to be obtained.

EXAMPLE 3

For immunofluorescence, each of the pre-washed, 100 microliter resuspensions of Example 2, which contained the antibody-labelled sperm, were treated with the appropriate secondary antibody in order to detect the presence of bound monoclonal or polyclonal antibodies to fibronectin. The F-1509 labelledsperm was treated with FITC-conjugated rabbit anti-goat IgG antibody per enclosed instructions as obtained from Jackson Immunoresearch in West Grove, PA. The A134 labelled sperm and the FN-15 labelled sperm were treated with a FITC-conjugated F(ab')$_2$ fragment of sheep anti-mouse IgG per enclosed instructions as obtained from Sigma Chemical Co. Each of the secondary antibodies was diluted to 1/20th of their original stock concentrations upon addition to the respective one hundred microliter samples. The antibody-labelled sperm were then incubated in the presence of the second antibody for one hour in the absence of light. Each sample was subsequently washed to remove any unbound secondary antibody using the wash protocol as described in Example 2 above. Each sample was resuspended to a concentration of $2-5 \times 10^6$ sperm/cc in PBS having 5mg/ml of BSA and evaluated for fluorescence using a 520 nm filter under UV illumination.

EXAMPLE 4

For immunobead binding, 0.5 mg of immunobeads coated with rabbit anti-mouse immunoglobulin, heavy and light chain specific (obtained from BioRad, Richmond, CA.), was washed in PBS containing 5 mg/ml of BSA and centrifuged at 6,000 rpm for 3 minutes. The wash step was repeated 4 times and the beads were resuspended in 1 milliliter of PBS with 5 mg/ml of BSA in preparation for contact with the monoclonal antibody-labelled sperm, the FN-15 labelled sperm and the A134 labelled sperm. Similarly, 8 mg of immunobeads coated with rabbit anti-goat immunoglobulin obtained from BioRad, was washed according to the wash protocol used for the rabbit anti-mouse immunobeads and subsequently resuspended in 1 milliliter of PBS with a BSA concentration of 10 mg/ml in preparation for contact with the polyclonal antibody-labelled sperm, F-1509 labelled sperm. Duplicate suspensions of the antibody-labelled sperm were prepared using the methods and materials set forth in Examples 1 and 2 above. Subsequently, a 100 microliter suspension of each of the 3 antibody/sperm complexes was pelleted by centrifugation and resuspended in BWW media with 5 mg/ml of HSA centrifugation of $5-10 \times 10^6$ cells/ml. Fifty microliters of beads and 5-10 microliters of sperm were mixed in a serologic tube, placed on a slide and observed within 10 minutes under phase contrast optics (640 x), in order to score sperm carrying beads. At least 100 motile sperm were scored. Only those sperm swimming within the bead suspension, observed to collide with immunobeads, were scored for bead binding.

Examples 3 and 4 are merely illustrative of two acceptable techniques known in the art which can be utilized in conjunction with the method of the present invention for detecting and determining the degree of fibronectin antibody binding as an indicator of capacitation. With respect to the techniques as applied in Examples 3 and 4, statistical analysis was performed as set forth below in Example 5 below.

EXAMPLE 5

The percent of spermatozoa displaying fibronectin on their surfaces in different experiments was expressed as a mean standard deviation (SD). Comparison of the results obtained with immunofluorescence an immunobead binding in the evaluation of anti-fibronectin antibody binding to spermatozoa was made using Student's "t" test for paired samples. No significant difference in the percent of sperm displaying fibronectin was found using immunofluorescence or immunobead binding. For F-1509, the mean $\pm$SD of sperm displaying fibronectin was $80.9 \pm 18.4\%$ and $68.8 \pm 33.7\%$ respectively for fertile donors and infertile patients as detected with IF (range 37-100% and 5-100%, median 83 and 79), and $75.1 \pm 21.8\%$ and $57.2 \pm 32.6\%$ with immunobead binding (range 24-95% and 6-100%, median 80 and 60). For FN-15, the mean $\pm$SD of sperm displaying fibronectin as detected with IF was $63.1 \pm 23.4\%$ and $62.3 \pm 25.7\%$ respectively for fertile donors and infertile patients (range 19-86% and 19-97%, mediam 68 and 65), and $55.7 \pm 15.9\%$ and $43.8 \pm 21.7\%$ with immunobead binding (range 28-74% and 11-81%, mediam 59.5 and 45). For A134, the mean $\pm$SD of sperm displaying fibronectin was $58.7 \pm 27.2\%$ and $70.8 \pm 28.8\%$ for fertile donors and infertile patients, respectively, (range 28-80% and 27-100%, median 68 and 82.5) as detected with IF, and $55.3 \pm 22.8\%$ and $66.4 \pm 27.1\%$, respectively, using immunobead binding (range 29-69% and 31-100%, median 68 and 69.5). Regional expression of fibronectin appeared to be predominantly on the sperm head, as detected by immunobeads. In contrast, differences in the region of fibronectin between spermatozoa from the same ejaculate were observed using immunofluorescence. The entire sperm surface was positive for the majority of spermatozoa (approximately 85%), while others showed an irregular fluorescence on their surfaces. Even when the entire sperm surface was fluorescent, some areas were brighter than others, varying for each spermatozoa without any particular regional association.

Although illustrated in terms of screening a sample of human sperm for a lack of capacitation based upon fibronectin expression, the method of the present invention, as provided by the methods and materials of Examples 1-5, can be readily adapted by those skilled in the art of immunology to provide for an effective method for evaluating the sperm of other mammalian species as well.

While there have been described what are presently believed to be the preferred embodiments of the present invention disclosed herein, those skilled in the art will realize that changes and modifications may be made thereto without departing from the spirit or the scope of the invention, and it is intended to claim all such changes and modifications as fall within the true scope of the invention.

what is claimed is:

1. A method for detecting the presence of infertility in a mammaliam male test animal comprising:
   potentiating a sample of spermatozoa obtained from said animal by subjecting it to conditions suitable for inducing capacitation of said sample; and
   contacting said sample to at least one of a polyclonal and a monoclonal antibody to fibronectin for a sufficient period of time and under conditions suitable to permit binding of said antibody with said sample in order to determine the extent of antibody binding, wherein a relative increase in antibody binding is indicative of whether the sperm has undergone capacitation and wherein a lack of antibody binding is ndicative of the absence of fertility.

2. The method according to claim 1 further comprising the step of obtaining a semen sample from said animal and subsequently separating and isolating seprmatozoa from said semen sample.

3. The method according to claim 1 wherein said mammaliam male test animal is a human.

4. The method according to claim 3 wherein said one of said polyclonal and said monoclonal antibody exhibits antibody binding to human fibronectin.

5. The method according to claim 3 wherein said one of said polyclonal and said nonclonal antibody is selected from the group consisting of F-1509, IgGl FN-15 and A134.

6. A method for detecting the inability of a sample of mammaliam spermatoxoa to undergo capacitation comprising:
   potentiating a sample of spermatozoa obtained from said animal by subjecting it to conditions suitable for inducing capacitiation of said sample; and
   contacting said sample to at least one of a polyclonal and a monoclonal antibody to fibronectin for a sufficient period of time and under conditions suitable to permit binding of said antibody with said sample in order to determine the extent of antibody binding, wherein a relative increase in antibody binding is indicative of whether the sperm has undergone capacitation and wherein a lack of binding is indicative of the absence of capacitation.

7. The method according to claim 6 further comprising the step of obtaining a semen sample from said animal and subsequently separating and isolating spermatozoa from said semen sample.

8. The method according to claim 6 wherein said mammaliam male test animal is a human.

9. the method according to claim 8 wherein said one of said polyclonal and said monoclonal antibody exhibits antibody binding to human fibronectin.

10. The method according to claim 8 wherein said one of said polyclonal and said monoclonal antibody is selected from the group consisting of F-1509 IgGl FN-15 and A134.

* * * * *